(12) United States Patent
Matsumura et al.

(10) Patent No.: US 10,995,160 B2
(45) Date of Patent: May 4, 2021

(54) PROTEIN AGGREGATION INHIBITOR

(71) Applicants: OSAKA ORGANIC CHEMICAL INDUSTRY LTD., Osaka (JP); JAPAN ADVANCED INSTITUTE OF SCIENCE AND TECHNOLOGY, Nomi (JP)

(72) Inventors: Kazuaki Matsumura, Nomi (JP); Rajan Robin, Nomi (JP); Yoko Taniyama, Hakusan (JP); Yoshiyuki Saruwatari, Osaka (JP)

(73) Assignees: OSAKA ORGANIC CHEMICAL INDUSTRY LTD., Osaka (JP); JAPAN ADVANCED INSTITUTE OF SCIENCE AND TECHNOLOGY, Nomi (JP)

( * ) Notice: Subject to any disclaimer, the term of this patent is extended or adjusted under 35 U.S.C. 154(b) by 239 days.

(21) Appl. No.: 16/313,405

(22) PCT Filed: Jun. 29, 2017

(86) PCT No.: PCT/JP2017/023879
§ 371 (c)(1),
(2) Date: Dec. 26, 2018

(87) PCT Pub. No.: WO2018/003909
PCT Pub. Date: Jan. 4, 2018

(65) Prior Publication Data
US 2019/0161563 A1 May 30, 2019

(30) Foreign Application Priority Data
Jun. 30, 2016 (JP) .............................. JP2016-130596

(51) Int. Cl.
*C08F 8/42* (2006.01)
*C08F 120/60* (2006.01)

(52) U.S. Cl.
CPC .............. *C08F 8/42* (2013.01); *C08F 120/60* (2013.01)

(58) Field of Classification Search
CPC . C08F 120/60; C08F 8/42; C12N 9/96; A61K 38/00
See application file for complete search history.

(56) References Cited

U.S. PATENT DOCUMENTS

2018/0118859 A1  5/2018  Matsumura et al.

FOREIGN PATENT DOCUMENTS

JP  2006-343201 A  12/2006
WO  WO 2016/181975 A1  11/2016

OTHER PUBLICATIONS

Durand-Gasselin et al., "Colloidal stability of zwitterionic polymer-grafted gold nanoparticles in water," *J. Colloid and Interface Sci.*, 434: 188-194 (2014).
Rajan et al., "A zwitterionic polymer as a novel inhibitor of protein aggregation," *J. Mater. Chem. B*, 3: 5683-5689 (2015).
Japanese Patent Office, International Search Report in International Patent Application No. PCT/JP2017/023879 (dated Sep. 26, 2017).

*Primary Examiner* — Mark S Kaucher
(74) *Attorney, Agent, or Firm* — Leydig, Voit & Mayer, Ltd.

(57) ABSTRACT

The present invention provides a protein aggregation inhibitor for use in preventing aggregation of a protein, which contains a terminal sulfanyl group-containing sulfobetaine polymer having a repeat unit derived from a sulfobetaine monomer represented by the formula (II), and a noble metal particle, and in which the terminal sulfanyl group-containing sulfobetaine polymer is chemisorbed on the noble metal particle by the sulfanyl group (the groups in the following formula are as defined in the DESCRIPTION).

$$H_2C=\underset{R^1}{\underset{|}{C}}-\underset{\underset{O}{\|}}{C}-X-R^2-\underset{\underset{R^4}{|}}{N^+}-R^5-\underset{\underset{O}{\|}}{\overset{\overset{O}{\|}}{S}}-O^- \quad (II)$$

20 Claims, No Drawings

PROTEIN AGGREGATION INHIBITOR

CROSS-REFERENCE TO RELATED APPLICATIONS

This patent application is the U.S. national phase of International Patent Application No. PCT/JP2017/023879, filed Jun. 29, 2017, which claims the benefit of Japanese Patent Application No. 2016-130596, filed on Jun. 30, 2016, which are incorporated by reference in their entireties herein.

TECHNICAL FIELD

The present invention relates to a protein aggregation inhibitor. The protein aggregation inhibitor of the present invention maintains lysozyme activity and prevents aggregation of protein even without using a surfactant. Thus, use thereof for various applications where inhibition of protein aggregation is desired such as preservative for enzyme, antibody drug, in vivo amyloid aggregation inhibitor and the like is expected.

BACKGROUND ART

As a protein aggregation inhibitor capable of preventing aggregation of protein under acidic conditions, a protein aggregation inhibitor containing at least one kind of non-ionic surfactant selected from the group consisting of polyoxyethylene distyrenated phenyl ether, polyoxyethylene myristyl ether and polyoxyethylene(10) octylphenyl ether has been proposed (e.g., patent document 1).

Since the aforementioned protein aggregation inhibitor can inhibit, to some extent, aggregation of protein under acidic conditions since it uses a surfactant.

When a surfactant is contained in the protein aggregation inhibitor, the use of the protein aggregation inhibitor is restricted. In recent years, therefore, the development of a protein aggregation inhibitor superior in the protein aggregation inhibitory effect even without using a surfactant has been desired.

DOCUMENT LIST

Patent Documents patent document 1: JP-A-2006-343201

SUMMARY OF THE INVENTION

Problems to be Solved by the Invention

The present invention has been made in view of the aforementioned prior art, and the problem thereof is provision of a protein aggregation inhibitor that maintains lysozyme activity and is superior in a protein aggregation inhibitory effect even without using a surfactant.

Means of Solving the Problems

The present invention relates to the following.
[1] A protein aggregation inhibitor for use in preventing aggregation of a protein, the inhibitor comprising a terminal sulfanyl group-containing sulfobetaine polymer having a repeat unit derived from a sulfobetaine monomer represented by the formula (II):

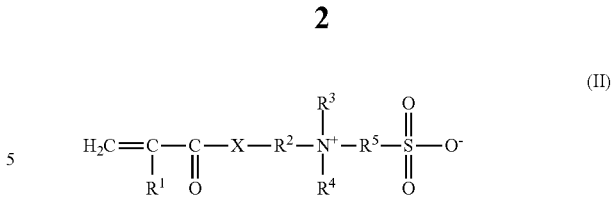

(in the formula (II), $R^1$ is a hydrogen atom or a methyl group, $R^2$ an alkyl group having 1-4 carbon atoms, $R^3$ and $R^4$ are each independently an alkyl group having 1-4 carbon atoms, $R^5$ is an alkyl group having 1-4 carbon atoms, and X is an —NH— group or an —O— group), and
a noble metal particle, wherein the terminal sulfanyl group-containing sulfobetaine polymer is chemisorbed on the noble metal particle by the sulfanyl group.
[2] The protein aggregation inhibitor of the aforementioned [1], wherein the terminal sulfanyl group-containing sulfobetaine polymer further has a carboxyl group.
[3] The protein aggregation inhibitor of the aforementioned [1] or [2], wherein the terminal sulfanyl group-containing sulfobetaine polymer is obtained by polymerizing monomer components comprising a sulfobetaine monomer represented by the formula (II) and a compound represented by the formula (III):

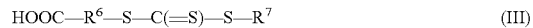

(in the formula (III), $R^6$ is an alkylene group having 1-8 carbon atoms and optionally having at least one substituent selected from the group consisting of a cyano group and a phenyl group, and $R^7$ is an alkyl group having 1-18 carbon atoms and optionally having at least one substituent selected from the group consisting of a carboxyl group and a phenyl group) to prepare a sulfobetaine polymer, and reducing the obtained sulfobetaine polymer.
[4] The protein aggregation inhibitor of the aforementioned [3], wherein $R^6$ is an alkylene group having 1-8 carbon atoms and optionally having a cyano group.
[5] The protein aggregation inhibitor of the aforementioned [3], wherein $R^6$ is an alkylene group having 1-8 carbon atoms.
[6] The protein aggregation inhibitor of the aforementioned [3], wherein $R^6$ is an alkylene group having 1-6 carbon atoms.
[7] The protein aggregation inhibitor of any one of the aforementioned [3] to [6], wherein $R^7$ is an alkyl group having 1-18 carbon atoms and optionally having a carboxyl group.
[8] The protein aggregation inhibitor of any one of the aforementioned [3] to [6], wherein $R^7$ is an alkyl group having 1-18 carbon atoms.
[9] The protein aggregation inhibitor of any one of the aforementioned [3] to [6], wherein $R^7$ is an alkyl group having 1-12 carbon atoms.
[10] The protein aggregation inhibitor of the aforementioned [3], wherein the compound represented by the formula (III) is at least one selected from the group consisting of 2-(dodecylthiocarbonothioylthio)-2-methylpropionic acid, 4-[(2-carboxyethylsulfanylthiocarbonyl)sulfanyl]-4-cyanopentanoic acid, 2-{[(2-carboxyethyl)sulfanylthiocarbonyl]sulfanyl}propanoic acid, 4-cyano-4-[(dodecylsulfanylthiocarbonyl)sulfanyl]pentanoic acid, and 2-[(dodecylsulfanylthiocarbonyl)sulfanyl]propanoic acid.
[11] The protein aggregation inhibitor of the aforementioned [3], wherein the compound represented by the formula (III) is 2-(dodecylthiocarbonothioylthio)-2-methylpropionic acid.

[12] The protein aggregation inhibitor of any one of the aforementioned [1] to [11], wherein the terminal sulfanyl group-containing sulfobetaine polymer has a weight average molecular weight of 3,000-140,000.
[13] The protein aggregation inhibitor of any one of the aforementioned [1] to [11], wherein the terminal sulfanyl group-containing sulfobetaine polymer has a weight average molecular weight of 4,000-70,000.
[14] The protein aggregation inhibitor of any one of the aforementioned [1] to [11], wherein the terminal sulfanyl group-containing sulfobetaine polymer has a weight average molecular weight of 4,500-56,000.
[15] The protein aggregation inhibitor of the aforementioned [1], wherein the terminal sulfanyl group-containing sulfobetaine polymer is represented by the formula (IV):

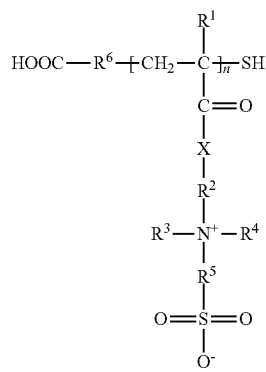

(IV)

(in the formula (IV), $R^1$ in the number of n are each independently a hydrogen atom or a methyl group, $R^2$ in the number of n are each independently an alkyl group having 1-4 carbon atoms, $R^3$ in the number of n are each independently an alkyl group having 1-4 carbon atoms, $R^4$ in the number of n are each independently an alkyl group having 1-4 carbon atoms, $R^5$ in the number of n are each independently an alkyl group having 1-4 carbon atoms, $R^6$ is an alkylene group having 1-8 carbon atoms and optionally having at least one substituent selected from the group consisting of a cyano group and a phenyl group, X in the number of n are each independently an —NH— group or an —O— group, and n is an average degree of polymerization of 10-500).
[16] The protein aggregation inhibitor of the aforementioned [15], wherein, in the formula (IV), $R^1$ is a hydrogen atom or a methyl group, $R^2$ is an alkyl group having 1-4 carbon atoms, $R^3$ and $R^4$ are each independently an alkyl group having 1-4 carbon atoms, $R^5$ is an alkyl group having 1-4 carbon atoms, $R^6$ is alkylene having 1-8 carbon atoms, and X is an —NH— group or an —O— group.
[17] The protein aggregation inhibitor of the aforementioned [15] or [16], wherein $R^6$ is an alkylene group having 1-8 carbon atoms and optionally having a cyano group.
[18] The protein aggregation inhibitor of the aforementioned [15] or [16], wherein $R^6$ is an alkylene group having 1-8 carbon atoms.
[19] The protein aggregation inhibitor of the aforementioned [15] or [16], wherein $R^6$ is an alkylene group having 1-6 carbon atoms.
[20] The protein aggregation inhibitor of any one of the aforementioned [15] to [19], wherein n is 15-400.
[21] The protein aggregation inhibitor of any one of the aforementioned [15] to [19], wherein n is 20-200.
[22] The protein aggregation inhibitor of any one of the aforementioned [1] to [21], wherein an amount of the terminal sulfanyl-group-containing sulfobetaine polymer is 5-60 parts by mass per 100 parts by mass of the noble metal particle.
[23] The protein aggregation inhibitor of any one of the aforementioned [1] to [21], wherein an amount of the terminal sulfanyl group-containing sulfobetaine polymer is 10-40 parts by mass per 100 parts by mass of the noble metal particle.
[24] A protein aggregation inhibitor for use in preventing aggregation of a protein, comprising a noble metal particle having, on its surface, a group represented by the formula (I):

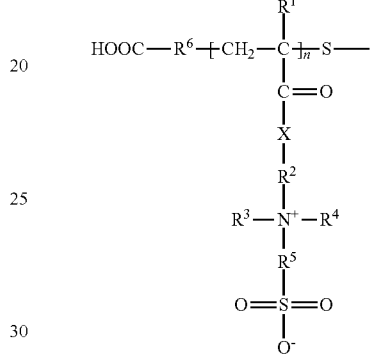

(I)

(in the formula (I), $R^1$ in the number of n are each independently a hydrogen atom or a methyl group, $R^2$ in the number of n are each independently an alkyl group having 1-4 carbon atoms, $R^3$ in the number of n are each independently an alkyl group having 1-4 carbon atoms, $R^4$ in the number of n are each independently an alkyl group having 1-4 carbon atoms, $R^5$ in the number of n are each independently an alkyl group having 1-4 carbon atoms, $R^6$ is an alkylene group having 1-8 carbon atoms and optionally having at least one substituent selected from the group consisting of a cyano group and a phenyl group, X in the number of n are each independently an —NH— group or an —O— group, and n is an average degree of polymerization of 10-500).
[25] The protein aggregation inhibitor of the aforementioned [24], wherein, in the formula (I), $R^1$ is a hydrogen atom or a methyl group, $R^2$ an alkyl group having 1-4 carbon atoms, $R^3$ and $R^4$ are each independently an alkyl group having 1-4 carbon atoms, $R^5$ is an alkyl group having 1-4 carbon atoms, $R^6$ is alkylene having 1-8 carbon atoms, and X is an —NH— group or an —O— group.
[26] The protein aggregation inhibitor of the aforementioned [24] or [25], wherein $R^6$ is an alkylene group having 1-8 carbon atoms and optionally having a cyano group.
[27] The protein aggregation inhibitor of the aforementioned [24] or [25], wherein $R^6$ is an alkylene group having 1-8 carbon atoms.
[28] The protein aggregation inhibitor of the aforementioned [24] or [25], wherein $R^6$ is an alkylene group having 1-6 carbon atoms.
[29] The protein aggregation inhibitor of any one of the aforementioned [24] to [28], wherein n is 15-400.
[30] The protein aggregation inhibitor of any one of the aforementioned [24] to [28], wherein n is 20-200.
[31] The protein aggregation inhibitor of any one of the aforementioned [24] to [30], wherein an amount of the group represented by the formula (I) is 5-60 parts by mass per 100 parts by mass of the noble metal particle.

[32] The protein aggregation inhibitor of any one of the aforementioned [24] to [30], wherein an amount of the group represented by the formula (I) is 10-40 parts by mass per 100 parts by mass of the noble metal particle parts by mass.

[33] The protein aggregation inhibitor of any one of the aforementioned [1] to [32], wherein $R^1$ is a hydrogen atom.

[34] The protein aggregation inhibitor of any one of the aforementioned [1] to [33], wherein $R^2$ is a —$(CH_2)$— group, a —$(CH_2)_2$— group or a —$(CH_2)_3$— group.

[35] The protein aggregation inhibitor of any one of the aforementioned [1] to [33], wherein $R^2$ is a —$(CH_2)_3$— group.

[36] The protein aggregation inhibitor of any one of the aforementioned [1] to [35], wherein $R^3$ is a methyl group, an ethyl group or a propyl group.

[37] The protein aggregation inhibitor of any one of the aforementioned [1] to [35], wherein $R^3$ is a methyl group or an ethyl group.

[38] The protein aggregation inhibitor of any one of the aforementioned [1] to [35], wherein $R^3$ is a methyl group.

[39] The protein aggregation inhibitor of any one of the aforementioned [1] to [38], wherein $R^4$ is a methyl group, an ethyl group or a propyl group.

[40] The protein aggregation inhibitor of any one of the aforementioned [1] to [38], wherein $R^4$ is a methyl group or an ethyl group.

[41] The protein aggregation inhibitor of any one of the aforementioned [1] to [38], wherein $R^4$ is a methyl group.

[42] The protein aggregation inhibitor of any one of the aforementioned [1] to [41], wherein $R^5$ is a —$(CH_2)$— group, a —$(CH_2)_2$— group or a —$(CH_2)_3$— group.

[43] The protein aggregation inhibitor of any one of the aforementioned [1] to [41], wherein $R^5$ is a —$(CH_2)_3$— group.

[44] The protein aggregation inhibitor of any one of the aforementioned [1] to [43], wherein X is an —NH— group.

[45] The protein aggregation inhibitor of any one of the aforementioned [1] to [44], wherein the noble metal is gold, platinum or silver.

[46] The protein aggregation inhibitor of any one of the aforementioned [1] to [44], wherein the noble metal is gold.

[47] The protein aggregation inhibitor of any one of the aforementioned [1] to [46], wherein the noble metal particle has an average particle size of 1-100 nm.

[48] The protein aggregation inhibitor of any one of the aforementioned [1] to [46], wherein the noble metal particle has an average particle size of 1-20 nm.

[49] The protein aggregation inhibitor of any one of the aforementioned [1] to [46], wherein the noble metal particle has an average particle size of 1-10 nm.

[50] A method for producing a protein aggregation inhibitor for use in preventing aggregation of a protein, the method comprising
polymerizing monomer components comprising a sulfobetaine monomer represented by the aforementioned formula (II) and a compound represented by the aforementioned formula (III) to prepare a sulfobetaine polymer,
reducing the obtained sulfobetaine polymer to prepare a terminal sulfanyl group-containing sulfobetaine polymer, and
mixing the obtained terminal sulfanyl group-containing sulfobetaine polymer and a noble metal particle.

[51] The method of the aforementioned [50], wherein an amount of the compound represented by the formula (III) is 0.01-0.5 mol per 1 mol of the sulfobetaine monomer represented by the formula (II).

[52] The method of the aforementioned [50], wherein an amount of the compound represented by the formula (III) is 0.03-0.3 mol per 1 mol of the sulfobetaine monomer represented by the formula (II).

[53] The method of any one of the aforementioned [50] to [52], wherein an amount of the noble metal particle is 10-100 parts by mass per 100 parts by mass of the terminal sulfanyl group-containing sulfobetaine polymer.

[54] The method of any one of the aforementioned [50] to [52], wherein an amount of the noble metal particle is 20-70 parts by mass per 100 parts by mass of the terminal sulfanyl group-containing sulfobetaine polymer.

[55] A method for preventing aggregation of a protein, comprising mixing the protein, a solvent or dispersion medium, and the protein aggregation inhibitor of any one of the aforementioned [1] to [49].

[56] The method of the aforementioned [55], wherein the protein aggregation inhibitor is used such that an amount of the noble metal particle with the terminal sulfanyl group-containing sulfobetaine polymer chemisorbed thereon or an amount of the noble metal particle having a group represented by the formula (I) on the surface is 0.01-10 parts by mass per 1 part by mass of the protein.

[57] The method of the aforementioned [55], wherein the protein aggregation inhibitor is used such that an amount of the noble metal particle with the terminal sulfanyl group-containing sulfobetaine polymer chemisorbed thereon or an amount of the noble metal particle having a group represented by the formula (I) on the surface is 0.1-1 parts by mass per 1 part by mass of the protein.

[58] The method of any one of the aforementioned [55] to [57], wherein the protein, the solvent or dispersion medium, and the protein aggregation inhibitor are mixed such that a content of the protein in the mixture comprising the protein, the solvent or dispersion medium, and the protein aggregation inhibitor is 0.001-20 mass %.

[59] The method of any one of the aforementioned [55] to [57], wherein the protein, the solvent or dispersion medium, and the protein aggregation inhibitor are mixed such that a content of the protein in the mixture comprising the protein, the solvent or dispersion medium, and the protein aggregation inhibitor is 0.01-10 mass %.

Effect of the Invention

According to the present invention, a protein aggregation inhibitor that maintains lysozyme activity and is superior in a protein aggregation inhibitory effect is provided even without using a surfactant.

DESCRIPTION OF EMBODIMENTS

The protein aggregation inhibitor of the present invention contains a terminal sulfanyl group-containing sulfobetaine polymer and noble metal particles, and is characterized in that the terminal sulfanyl group-containing sulfobetaine polymer is chemisorbed on the noble metal particles by the sulfanyl group. As used herein, chemisorption means that a sulfur atom of the sulfanyl group (—SH) of the terminal sulfanyl group-containing sulfobetaine polymer forms a coordinate bond with noble metal particles, or a hydrogen atom is dissociated from the sulfanyl group, and the sulfur atom and the noble metal particles form a covalent bond.

The terminal sulfanyl group-containing sulfobetaine polymer has a repeat unit derived from a sulfobetaine monomer represented by the formula (II):

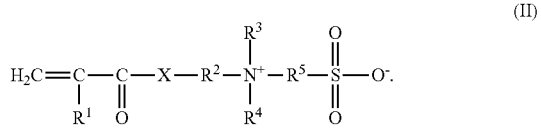

The aforementioned repeat unit may be only one kind or include two or more kinds.

In the formula (II), $R^1$ is a hydrogen atom or a methyl group, preferably a hydrogen atom.

$R^2$ is an alkyl group having 1-4 carbon atoms. In the present invention, the alkylene group may be a linear or branched chain. The same applies to the alkylene group described below. Examples of the alkylene group having 1-4 carbon atoms include a methylene group ($-CH_2-$), an ethylene group ($-(CH_2)_2-$), a propylene group (e.g., $-(CH_2)_3-$) and a butylene group (e.g., $-(CH_2)_4-$). Among these groups, a methylene group, an ethylene group and a propylene group are preferable, a $-(CH_2)-$ group, a $-(CH_2)_2-$ group and a $-(CH_2)_3-$ group are more preferable, and a $-(CH_2)_3-$ group is further preferable for obtaining a protein aggregation inhibitor that maintains lysozyme activity and is superior in a protein aggregation inhibitory effect.

$R^3$ and $R^4$ are each independently an alkyl group having 1-4 carbon atoms. In the present invention, the alkyl group may be a linear or branched chain. The same applies to the alkyl group described below. Examples of the alkyl group having 1-4 carbon atoms include a methyl group, an ethyl group, a propyl group and a butyl group. Among these groups, a methyl group, an ethyl group and a propyl group are preferable, a methyl group and an ethyl group are more preferable, and a methyl group is further preferable for obtaining a protein aggregation inhibitor that maintains lysozyme activity and is superior in a protein aggregation inhibitory effect.

$R^5$ is an alkylene group having 1-4 carbon atoms. Examples of the alkylene group having 1-4 carbon atoms include a methylene group ($-(CH_2)-$), an ethylene group ($-(CH_2)_2-$), a propylene group (e.g., $-(CH_2)_3-$) and a butylene group (e.g., $-(CH_2)_4-$). Among these groups, a methylene group, an ethylene group and a propylene group are preferable, a $-(CH_2)-$ group, a $-(CH_2)_2-$ group and a $-(CH_2)_3-$ group are more preferable, and a $-(CH_2)_3-$ group is further preferable for obtaining a protein aggregation inhibitor that maintains lysozyme activity and is superior in a protein aggregation inhibitory effect.

X is an $-NH-$ group or an $-O-$ group. Of these groups, an $-NH-$ group is preferable for obtaining a protein aggregation inhibitor that maintains lysozyme activity and is superior in a protein aggregation inhibitory effect.

Examples of the sulfobetaine monomer represented by the formula (II) include 3-[(3-(meth)acrylamidoalkyl)dialkylammonio]alkane-1-sulfonates such as 3-[(3-acrylamidomethyl)dimethylammonio]ethane-1-sulfonate, 3-[(3-methacrylamidomethyl)dimethylammonio]ethane-1-sulfonate, 3-[(3-acrylamidomethyl)diethylammonio]ethane-1-sulfonate, 3-[(3-methacrylamidomethyl)diethylammonio]ethane-1-sulfonate, 3-[(3-acrylamidomethyl)dipropylammonio]ethane-1-sulfonate, 3-[(3-methacrylamidomethyl)dipropylammonio]ethane-1-sulfonate, 3-[(3-acrylamidomethyl)dibutylammonio]ethane-1-sulfonate, 3-[(3-methacrylamidomethyl)dibutylammonio]ethane-1-sulfonate, 3-[(3-acrylamidoethyl)dimethylammonio]ethane-1-sulfonate, 3-[(3-methacrylamidoethyl)dimethylammonio]ethane-1-sulfonate, 3-[(3-acrylamidoethyl)diethylammonio]ethane-1-sulfonate, 3-[(3-methacrylamidoethyl)diethylammonio]ethane-1-sulfonate, 3-[(3-acrylamidoethyl)dipropylammonio]ethane-1-sulfonate, 3-[(3-methacrylamidoethyl)dipropylammonio]ethane-1-sulfonate, 3-[(3-acrylamidoethyl)dibutylammonio]ethane-1-sulfonate, 3-[(3-methacrylamidoethyl)dibutylammonio]ethane-1-sulfonate, 3-[(3-acrylamidopropyl)dimethylammonio]ethane-1-sulfonate, 3-[(3-methacrylamidopropyl)dimethylammonio]ethane-1-sulfonate, 3-[(3-acrylamidopropyl)diethylammonio]ethane-1-sulfonate, 3-[(3-methacrylamidopropyl)diethylammonio]ethane-1-sulfonate, 3-[(3-acrylamidopropyl)dipropylammonio]ethane-1-sulfonate, 3-[(3-methacrylamidopropyl)dipropylammonio]ethane-1-sulfonate, 3-[(3-acrylamidopropyl)dibutylammonio]ethane-1-sulfonate, 3-[(3-methacrylamidopropyl)dibutylammonio]ethane-1-sulfonate, 3-[(3-acrylamidobutyl)dimethylammonio]ethane-1-sulfonate, 3-[(3-methacrylamidobutyl)dimethylammonio]ethane-1-sulfonate, 3-[(3-acrylamidobutyl)diethylammonio]ethane-1-sulfonate, 3-[(3-methacrylamidobutyl)diethylammonio]ethane-1-sulfonate, 3-[(3-acrylamidobutyl)dipropylammonio]ethane-1-sulfonate, 3-[(3-methacrylamidobutyl)dipropylammonio]ethane-1-sulfonate, 3-[(3-acrylamidobutyl)dibutylammonio]ethane-1-sulfonate, 3-[(3-methacrylamidobutyl)dibutylammonio]ethane-1-sulfonate, 3-[(3-acrylamidomethyl)dimethylammonio]propane-1-sulfonate, 3-[(3-methacrylamidomethyl)dimethylammonio]propane-1-sulfonate, 3-[(3-acrylamidomethyl)diethylammonio]propane-1-sulfonate, 3-[(3-methacrylamidomethyl)diethylammonio]propane-1-sulfonate, 3-[(3-acrylamidomethyl)dipropylammonio]propane-1-sulfonate, 3-[(3-methacrylamidomethyl)dipropylammonio]propane-1-sulfonate, 3-[(3-acrylamidomethyl)dibutylammonio]propane-1-sulfonate, 3-[(3-methacrylamidomethyl)dibutylammonio]propane-1-sulfonate, 3-[(3-acrylamidoethyl)dimethylammonio]propane-1-sulfonate, 3-[(3-methacrylamidoethyl)dimethylammonio]propane-1-sulfonate, 3-[(3-acrylamidoethyl)diethylammonio]propane-1-sulfonate, 3-[(3-methacrylamidoethyl)diethylammonio]propane-1-sulfonate, 3-[(3-acrylamidoethyl)dipropylammonio]propane-1-sulfonate, 3-[(3-methacrylamidoethyl)dipropylammonio]propane-1-sulfonate, 3-[(3-acrylamidoethyl)dibutylammonio]propane-1-sulfonate, 3-[(3-methacrylamidoethyl)dibutylammonio]propane-1-sulfonate, 3-[(3-acrylamidopropyl)dimethylammonio]propane-1-sulfonate, 3-[(3-methacrylamidopropyl)dimethylammonio]propane-1-sulfonate, 3-[(3-acrylamidopropyl)diethylammonio]propane-1-sulfonate, 3-[(3-methacrylamidopropyl)diethylammonio]propane-1-sulfonate, 3-[(3-acrylamidopropyl)dipropylammonio]propane-1-sulfonate, 3-[(3-methacrylamidopropyl)dipropylammonio]propane-1-sulfonate, 3-[(3-acrylamidopropyl)dibutylammonio]propane-1-sulfonate, 3-[(3-methacrylamidopropyl)dibutylammonio]propane-1-sulfonate, 3-[(3-acrylamidobutyl)dimethylammonio]propane-1-sulfonate, 3-[(3-methacrylamidobutyl)dimethylammonio]propane-1-sulfonate, 3-[(3-acrylamidobutyl)diethylammonio]propane-1-sulfonate, 3-[(3-methacrylamidobutyl)diethylammonio]propane-1-sulfonate, 3-[(3-acrylamidobutyl)

dipropylammonio]propane-1-sulfonate, 3-[(3-methacrylamidobutyl)dipropylammonio]propane-1-sulfonate, 3-[(3-acrylamidobutyl)dibutylammonio]propane-1-sulfonate, 3-[(3-methacrylamidobutyl)dibutylammonio]propane-1-sulfonate, 3-[(3-acrylamidomethyl)dimethylammonio]butane-1-sulfonate, 3-[(3-methacrylamidomethyl)dimethylammonio]butane-1-sulfonate, 3-[(3-acrylamidomethyl)diethylammonio]butane-1-sulfonate, 3-[(3-methacrylamidomethyl)diethylammonio]butane-1-sulfonate, 3-[(3-acrylamidomethyl)dipropylammonio]butane-1-sulfonate, 3-[(3-methacrylamidomethyl)dipropylammonio]butane-1-sulfonate, 3-[(3-acrylamidomethyl)dibutylammonio]butane-1-sulfonate, 3-[(3-methacrylamidomethyl)dibutylammonio]butane-1-sulfonate, 3-[(3-acrylamidoethyl)dimethylammonio]butane-1-sulfonate, 3-[(3-methacrylamidoethyl)dimethylammonio]butane-1-sulfonate, 3-[(3-acrylamidoethyl)diethylammonio]butane-1-sulfonate, 3-[(3-methacrylamidoethyl)diethylammonio]butane-1-sulfonate, 3-[(3-acrylamidoethyl)dipropylammonio]butane-1-sulfonate, 3-[(3-methacrylamidoethyl)dipropylammonio]butane-1-sulfonate, 3-[(3-acrylamidoethyl)dibutylammonio]butane-1-sulfonate, 3-[(3-methacrylamidoethyl)dibutylammonio]butane-1-sulfonate, 3-[(3-acrylamidopropyl)dimethylammonio]butane-1-sulfonate, 3-[(3-methacrylamidopropyl)dimethylammonio]butane-1-sulfonate, 3-[(3-acrylamidopropyl)diethylammonio]butane-1-sulfonate, 3-[(3-methacrylamidopropyl)diethylammonio]butane-1-sulfonate, 3-[(3-acrylamidopropyl)dipropylammonio]butane-1-sulfonate, 3-[(3-methacrylamidopropyl)dipropylammonio]butane-1-sulfonate, 3-[(3-acrylamidopropyl)dibutylammonio]butane-1-sulfonate, 3-[(3-methacrylamidopropyl)dibutylammonio]butane-1-sulfonate, 3-[(3-acrylamidobutyl)dimethylammonio]butane-1-sulfonate, 3-[(3-methacrylamidobutyl)dimethylammonio]butane-1-sulfonate, 3-[(3-acrylamidobutyl)diethylammonio]butane-1-sulfonate, 3-[(3-methacrylamidobutyl)diethylammonio]butane-1-sulfonate, 3-[(3-acrylamidobutyl)dipropylammonio]butane-1-sulfonate, 3-[(3-methacrylamidobutyl)dipropylammonio]butane-1-sulfonate, 3-[(3-acrylamidobutyl)dibutylammonio]butane-1-sulfonate, 3-[(3-methacrylamidobutyl)dibutylammonio]butane-1-sulfonate and the like;

3-[(3-(meth)acryloyloxyalkyl)dialkylammonio]alkane-1-sulfonates such as 3-[(3-acryloyloxymethyl)dimethylammonio]ethane-1-sulfonate, 3-[(3-methacryloyloxymethyl)dimethylammonio]ethane-1-sulfonate, 3-[(3-acryloyloxymethyl)diethylammonio]ethane-1-sulfonate, 3-[(3-methacryloyloxymethyl)diethylammonio]ethane-1-sulfonate, 3-[(3-acryloyloxymethyl)dipropylammonio]ethane-1-sulfonate, 3-[(3-methacryloyloxymethyl)dipropylammonio]ethane-1-sulfonate, 3-[(3-acryloyloxymethyl)dibutylammonio]ethane-1-sulfonate, 3-[(3-methacryloyloxymethyl)dibutylammonio]ethane-1-sulfonate, 3-[(3-acryloyloxyethyl)dimethylammonio]ethane-1-sulfonate, 3-[(3-methacryloyloxyethyl)dimethylammonio]ethane-1-sulfonate, 3-[(3-acryloyloxyethyl)diethylammonio]ethane-1-sulfonate, 3-[(3-methacryloyloxyethyl)diethylammonio]ethane-1-sulfonate, 3-[(3-acryloyloxyethyl)dipropylammonio]ethane-1-sulfonate, 3-[(3-methacryloyloxyethyl)dipropylammonio]ethane-1-sulfonate, 3-[(3-acryloyloxyethyl)dibutylammonio]ethane-1-sulfonate, 3-[(3-methacryloyloxyethyl)dibutylammonio]ethane-1-sulfonate, 3-[(3-acryloyloxypropyl)dimethylammonio]ethane-1-sulfonate, 3-[(3-methacryloyloxypropyl)dimethylammonio]ethane-1-sulfonate, 3-[(3-acryloyloxypropyl)diethylammonio]ethane-1-sulfonate, 3-[(3-methacryloyloxypropyl)diethylammonio]ethane-1-sulfonate, 3-[(3-acryloyloxypropyl)dipropylammonio]ethane-1-sulfonate, 3-[(3-methacryloyloxypropyl)dipropylammonio]ethane-1-sulfonate, 3-[(3-acryloyloxypropyl)dibutylammonio]ethane-1-sulfonate, 3-[(3-methacryloyloxypropyl)dibutylammonio]ethane-1-sulfonate, 3-[(3-acryloyloxybutyl)dimethylammonio]ethane-1-sulfonate, 3-[(3-methacryloyloxybutyl)dimethylammonio]ethane-1-sulfonate, 3-[(3-acryloyloxybutyl)diethylammonio]ethane-1-sulfonate, 3-[(3-methacryloyloxybutyl)diethylammonio]ethane-1-sulfonate, 3-[(3-acryloyloxybutyl)dipropylammonio]ethane-1-sulfonate, 3-[(3-methacryloyloxybutyl)dipropylammonio]ethane-1-sulfonate, 3-[(3-acryloyloxybutyl)dibutylammonio]ethane-1-sulfonate, 3-[(3-methacryloyloxybutyl)dibutylammonio]ethane-1-sulfonate, 3-[(3-acryloyloxymethyl)dimethylammonio]propane-1-sulfonate, 3-[(3-methacryloyloxymethyl)dimethylammonio]propane-1-sulfonate, 3-[(3-acryloyloxymethyl)diethylammonio]propane-1-sulfonate, 3-[(3-methacryloyloxymethyl)diethylammonio]propane-1-sulfonate, 3-[(3-acryloyloxymethyl)dipropylammonio]propane-1-sulfonate, 3-[(3-methacryloyloxymethyl)dipropylammonio]propane-1-sulfonate, 3-[(3-acryloyloxymethyl)dibutylammonio]propane-1-sulfonate, 3-[(3-methacryloyloxymethyl)dibutylammonio]propane-1-sulfonate, 3-[(3-acryloyloxyethyl)dimethylammonio]propane-1-sulfonate, 3-[(3-methacryloyloxyethyl)dimethylammonio]propane-1-sulfonate, 3-[(3-acryloyloxyethyl)diethylammonio]propane-1-sulfonate, 3-[(3-methacryloyloxyethyl)diethylammonio]propane-1-sulfonate, 3-[(3-acryloyloxyethyl)dipropylammonio]propane-1-sulfonate, 3-[(3-methacryloyloxyethyl)dipropylammonio]propane-1-sulfonate, 3-[(3-acryloyloxyethyl)dibutylammonio]propane-1-sulfonate, 3-[(3-methacryloyloxyethyl)dibutylammonio]propane-1-sulfonate, 3-[(3-acryloyloxypropyl)dimethylammonio]propane-1-sulfonate, 3-[(3-methacryloyloxypropyl)dimethylammonio]propane-1-sulfonate, 3-[(3-acryloyloxypropyl)diethylammonio]propane-1-sulfonate, 3-[(3-methacryloyloxypropyl)diethylammonio]propane-1-sulfonate, 3-[(3-acryloyloxypropyl)dipropylammonio]propane-1-sulfonate, 3-[(3-methacryloyloxypropyl)dipropylammonio]propane-1-sulfonate, 3-[(3-acryloyloxypropyl)dibutylammonio]propane-1-sulfonate, 3-[(3-methacryloyloxypropyl)dibutylammonio]propane-1-sulfonate, 3-[(3-acryloyloxybutyl)dimethylammonio]propane-1-sulfonate, 3-[(3-methacryloyloxybutyl)dimethylammonio]propane-1-sulfonate, 3-[(3-acryloyloxybutyl)diethylammonio]propane-1-sulfonate, 3-[(3-methacryloyloxybutyl)diethylammonio]propane-1-sulfonate, 3-[(3-acryloyloxybutyl)dipropylammonio]propane-1-sulfonate, 3-[(3-methacryloyloxybutyl)dipropylammonio]propane-1-sulfonate, 3-[(3-acryloyloxybutyl)dibutylammonio]propane-1-sulfonate, 3-[(3-methacryloyloxybutyl)dibutylammonio]propane-1-sulfonate, 3-[(3-acryloyloxymethyl)dimethylammonio]butane-1-sulfonate, 3-[(3-methacryloyloxymethyl)dimethylammonio]butane-1-sulfonate, 3-[(3-acryloyloxymethyl)diethylammonio]butane-1-sulfonate, 3-[(3-methacryloyloxymethyl)diethylammonio]butane-1-sulfonate, 3-[(3-acryloyloxymethyl)dipropylammonio]butane-1-sulfonate, 3-[(3-methacryloyloxymethyl)dipropylammonio]butane-1-sulfonate, 3-[(3-acryloyloxymethyl)dibutylammonio]butane-1-sulfonate, 3-[(3-methacryloyloxymethyl)

dibutylammonio]butane-1-sulfonate, 3-[(3-acryloyloxyethyl)dimethylammonio]butane-1-sulfonate, 3-[(3-methacryloyloxyethyl)dimethylammonio]butane-1-sulfonate, 3-[(3-acryloyloxyethyl)diethylammonio]butane-1-sulfonate, 3-[(3-methacryloyloxyethyl)diethylammonio]butane-1-sulfonate, 3-[(3-acryloyloxyethyl)dipropylammonio]butane-1-sulfonate, 3-[(3-methacryloyloxyethyl)dipropylammonio]butane-1-sulfonate, 3-[(3-acryloyloxyethyl)dibutylammonio]butane-1-sulfonate, 3-[(3-methacryloyloxyethyl)dibutylammonio]butane-1-sulfonate, 3-[(3-acryloyloxypropyl)dimethylammonio]butane-1-sulfonate, 3-[(3-methacryloyloxypropyl)dimethylammonio]butane-1-sulfonate, 3-[(3-acryloyloxypropyl)diethylammonio]butane-1-sulfonate, 3-[(3-methacryloyloxypropyl)diethylammonio]butane-1-sulfonate, 3-[(3-acryloyloxypropyl)dipropylammonio]butane-1-sulfonate, 3-[(3-methacryloyloxypropyl)dipropylammonio]butane-1-sulfonate, 3-[(3-acryloyloxypropyl)dibutylammonio]butane-1-sulfonate, 3-[(3-methacryloyloxypropyl)dibutylammonio]butane-1-sulfonate, 3-[(3-acryloyloxybutyl)dimethylammonio]butane-1-sulfonate, 3-[(3-methacryloyloxybutyl)dimethylammonio]butane-1-sulfonate, 3-[(3-acryloyloxybutyl)diethylammonio]butane-1-sulfonate, 3-[(3-methacryloyloxybutyl)diethylammonio]butane-1-sulfonate, 3-[(3-acryloyloxybutyl)dipropylammonio]butane-1-sulfonate, 3-[(3-methacryloyloxybutyl)dipropylammonio]butane-1-sulfonate, 3-[(3-acryloyloxybutyl)dibutylammonio]butane-1-sulfonate, 3-[(3-methacryloyloxybutyl)dibutylammonio]butane-1-sulfonate and the like; and the like. However, the present invention is not limited to these examples alone. These sulfobetaine monomers may each be used alone, or two or more kinds thereof may be used in combination.

In the present invention, "(meth)acrylamide" means acrylamide or methacrylamide, acrylamide and methacrylamide may each be used alone, or may be used in combination.

The "(meth)acryloyloxy" means acryloyloxy or methacryloyloxy, and acryloyloxy and methacryloyloxy may each be used alone, or may be used in combination.

The "(meth)acrylate" means acrylate or methacrylate, and acrylate and methacrylate may each be used alone, or may be used in combination.

The "(meth)acrylic acid" means acrylic acid or methacrylic acid, and acrylic acid and methacrylic acid may each be used alone, or may be used in combination.

As long as the object of the present invention is not inhibited, the terminal sulfanyl group-containing sulfobetaine polymer optionally has a repeat unit derived from other monomer different from the sulfobetaine monomer represented by the formula (II). Examples of other monomer include a water-soluble monomer.

The water-soluble monomer means a monomer showing dissolution property of not less than 50 g in 100 g of water at 25° C. Examples of the water-soluble monomer include (meth)acrylamide, N-vinylpyrrolidone, (methacrylonitrile, 2-hydroxyethyl (meth)acrylate, 2-hydroxypropyl (meth) acrylate, 4-hydroxybutyl (meth)acrylate, polyethylene glycol (meth)acrylate, methoxypolyethylene glycol (meth) acrylate, ethoxypolyethylene glycol (meth)acrylate, polyethylene glycol di(meth)acrylate, N-(meth)acrylmorpholide, N-methoxymethyl(meth)acrylamide, N-hydroxymethyl (meth)acrylamide, N-hydroxyethyl(meth)acrylamide, 2-hydroxyethyl vinyl ether, N,N-dimethyl(meth)acrylamide, N,N-diethyl(meth)acrylamide, N-monomethyl(meth)acrylamide, N-monoethyl(meth)acrylamide and the like. However, the present invention is not limited to these examples alone. These water-soluble monomers may each be used alone, or two or more kinds thereof may be used in combination. Among these water-soluble monomers, (meth) acrylamide, N-vinylpyrrolidone and (meth)acrylonitrile are preferable, and (meth)acrylamide and N-vinylpyrrolidone are more preferable for obtaining a protein aggregation inhibitor that maintains lysozyme activity and is superior in a protein aggregation inhibitory effect.

Examples of other monomer include a water-insoluble monomer. The water-insoluble monomer means a monomer showing dissolution property of less than 50 g in 100 g of water at 25° C.

Examples of the water-insoluble monomer include alkyl (meth) acrylate, alkoxy group-containing (meth) acrylate, alicyclic group-containing (meth)acrylate, aryl group-containing (meth)acrylate, aromatic monomer other than aryl group-containing (meth)acrylate and the like. However, the present invention is not limited to these examples alone. These water-insoluble monomers may each be used alone, or two or more kinds thereof may be used in combination.

Examples of the alkyl (meth)acrylate include methyl (meth)acrylate, ethyl (meth)acrylate, n-propyl (meth)acrylate, isopropyl (meth)acrylate, n-butyl (meth)acrylate, isobutyl (meth) acrylate, tert-butyl (meth) acrylate, sec-butyl (meth)acrylate, n-pentyl (meth)acrylate, n-hexyl (meth) acrylate, n-octyl (meth)acrylate, isooctyl (meth)acrylate, n-nonyl (meth) acrylate, isononyl (meth) acrylate, 2-ethylhexyl (meth)acrylate, decyl (meth)acrylate, dodecyl (meth) acrylate, tridecyl (meth)acrylate, tetradecyl (meth)acrylate, hexadecyl (meth)acrylate, octadecyl (meth)acrylate, isostearyl (meth)acrylate, eicosyl (meth)acrylate, behenyl (meth) acrylate, tetrahydrofurfuryl (meth)acrylate and the like. However, the present invention is not limited to these examples alone. These alkyl (meth)acrylates may each be used alone, or two or more kinds thereof may be used in combination.

Examples of the alkoxy group-containing (meth)acrylate include 2-methoxyethyl (meth) acrylate, 2-ethoxyethyl (meth) acrylate, methoxyethylene glycol (meth)acrylate, ethylcarbitol (meth)acrylate and the like. However, the present invention is not limited to these examples alone. These alkoxy group-containing (meth)acrylates may each be used alone, or two or more kinds thereof may be used in combination.

Examples of the alicyclic group-containing (meth)acrylate include cyclohexyl (meth) acrylate, tert-butylcyclohexyl (meth) acrylate, isobornyl (meth)acrylate, dicyclopentanyl (meth)acrylate, dicyclopentenyl (meth) acrylate, adamantyl (meth)acrylate, dicyclopentenyl (meth)acrylate, and the like. However, the present invention is not limited to these examples alone. These alicyclic group-containing (meth) acrylates may each be used alone, or two or more kinds thereof may be used in combination.

Examples of the aryl group-containing (meth)acrylate include (meth)acrylates having an aryl group having 6-15 carbon atoms, such as benzyl (meth)acrylate, phenoxyethyl (meth)acrylate and the like, and the like. However, the present invention is not limited to these examples alone. These aryl group-containing (meth)acrylates may each be used alone, or two or more kinds thereof may be used in combination.

Examples of the aromatic monomer other than aryl group-containing (meth)acrylate include styrene, α-methylstyrene and the like. However, the present invention is not limited to these examples alone. These aromatic monomers may each be used alone, or two or more kinds thereof may be used in combination.

The amount of the repeat unit derived from other monomer different from the sulfobetaine monomer represented by the formula (II) is preferably less than 50 mol %, more preferably less than 30 mol %, further preferably less than 10 mol %, relative to the amount of all repeat units derived from the sulfobetaine monomer represented by the formula (II) and other monomers.

Examples of a method of polymerizing monomer components including the sulfobetaine monomer represented by the formula (II) and other monomers as necessary include bulk polymerization method, solution polymerization method, emulsion polymerization method, suspension polymerization method and the like. However, the present invention is not limited to these examples alone. Of these polymerization methods, the solution polymerization method is preferable.

When monomer components are polymerized by the solution polymerization method, for example, the monomer components can be polymerized by dissolving the monomer components in an aqueous solvent, and adding a polymerization initiator to the obtained solution while stirring the solution. Alternatively, the monomer components can be polymerized by dissolving a polymerization initiator in an aqueous solvent, and adding monomer components to the obtained solution while stirring the solution.

The aqueous solvent is water or a mixed solvent of water and a hydrophilic organic solvent other than water. The content of water in the aqueous solvent is generally not less than 50 mass % and not more than 100 mass %.

Examples of the hydrophilic organic solvent include monovalent aliphatic alcohols having 1-4 carbon atoms such as methanol, ethanol, propanol and the like; ketones such as acetone, methyl ethyl ketone and the like; ethers such as tetrahydrofuran, dioxane, diglyme and the like; amides such as N,N-dimethylformamide, N,N-dimethylacetamide, N-methyl-2-pyrrolidone, 1,3-dimethyl-2-imidazolidinone and the like; sulfur-containing organic solvents such as dimethyl sulfoxide, sulfolane and the like, and the like. However, the present invention is not limited to these examples alone. These hydrophilic organic solvents may each be used alone, or two or more kinds thereof may be used in combination. Among these hydrophilic organic solvents, the monovalent aliphatic alcohols having 1-4 carbon atoms are preferable, methanol, ethanol and propanol are more preferable, methanol and ethanol are further preferable, for obtaining a protein aggregation inhibitor that maintains lysozyme activity and is superior in a protein aggregation inhibitory effect.

While the amount of the aqueous solvent is not particularly limited, it is generally preferably 50-400 parts by mass, more preferably 100-350 parts by mass, per 100 parts by mass of the monomer components.

When monomer components are polymerized, it is preferable to use a chain transfer agent to prepare the molecular weight of the obtained sulfobetaine polymer. Examples of the preferable chain transfer agent include a thiocarbonylthio group-containing compound having a carboxyl group and the like.

The thiocarbonylthio group-containing, compound having a carboxyl group is preferably a compound represented by the formula (III):

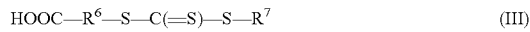

(in the formula (III), $R^6$ is an alkylene group having 1-8 carbon atoms and optionally having at least one substituent selected from the group consisting of a cyano group and a phenyl group, and $R^7$ is an alkyl group having 1-18 carbon atoms and optionally having at least one substituent selected from the group consisting of a carboxyl group and a phenyl group). The compound represented by the formula (III) may be used alone, or two or more kinds thereof may be used in combination.

Among those for $R^6$ in the formula (III), an alkylene group having 1-8 carbon atoms and optionally having a cyano group is preferable, an alkylene group having 1-8 carbon atoms is more preferably, an alkylene group having 1-6 carbon atoms is further preferable, for obtaining a protein aggregation inhibitor that maintains lysozyme activity and is superior in a protein aggregation inhibitory effect.

$R^7$ is preferably an alkyl group having 1-18 carbon atoms and optionally having a carboxyl group, more preferably an alkyl group having 1-18 carbon atoms, further preferably an alkyl group having 1-12 carbon atoms, for obtaining a protein aggregation inhibitor that maintains lysozyme activity and is superior in a protein aggregation inhibitory effect.

Examples of the compound represented by the formula (III) include 2-(dodecylthiocarbonothioylthio)-2-methylpropionic acid, 4-[(2-carboxyethylsulfanylthiocarbonyl)sulfanyl]-4-cyanopentanoic acid, 2-{[(2-carboxyethyl)sulfanylthiocarbonyl]sulfanyl}propanoic acid, 4-cyano-4-[(dodecylsulfanylthiocarbonyl)sulfanyl]pentanoic acid, 2-[(dodecylsulfanylthiocarbonyl)sulfanyl]propanoic acid, and the like. However, the present invention is not limited to these examples alone. These thiocarbonylthio group-containing compounds having a carboxyl group may each be used alone, or two or more kinds thereof may be used in combination Among these, 2-(dodecylthiocarbonothioylthio)-2-methylpropionic acid is preferable.

In the monomer components, the amount of the compound represented by the formula (III) is preferably 0.01-0.5 mol, more preferably 0.03-0.3 mol, per 1 mol of the sulfobetaine monomer represented by the formula (II), for obtaining a protein aggregation inhibitor that maintains lysozyme activity and is superior in a protein aggregation inhibitory effect.

It is preferable to polymerize monomer components containing a sulfobetaine monomer represented by the formula (II) and a compound represented by the formula (III) to prepare a sulfobetaine polymer, and reduce the obtained sulfobetaine monomer as mentioned below to produce the terminal sulfanyl group-containing sulfobetaine polymer.

The terminal sulfanyl group-containing sulfobetaine polymer optionally has a repeat unit derived from other monomer different from the sulfobetaine monomer represented by the formula (II). It is preferably composed of a repeat unit derived from the sulfobetaine monomer represented by the formula (II), the structure (HOOC—$R^6$—) derived from the thiocarbonylthio group-containing compound represented by the formula (III) and a sulfanyl group (—SH).

When the monomer components are polymerized, a polymerization initiator is preferably used. Examples of the polymerization initiator include azobisisobutyronitrile, azoisobutyronitrile, azo methyl isobutyrate, azobisdimethylvaleronitrile, benzoyl peroxide, potassium persulfate, ammonium persulfate, benzophenone derivative, phosphineoxide derivative, benzoketone derivative, phenyl thioether derivative, azide derivative, diazo derivative, disulfide derivative and the like. However, the present invention is not limited to these examples alone. These polymerization initiators may each be used alone, or two or more kinds thereof may be used in combination. While the amount of the polymerization initiator is not particularly limited, it is generally preferably about 0.05-20 parts by mass per 100 parts by mass of the monomer components.

The polymerization reaction temperature and atmosphere when the monomer components are polymerized are not particularly limited. Generally, the polymerization reaction temperature is about 50-120° C. The atmosphere at the time of polymerization reaction is preferably inert gas atmosphere such as nitrogen gas and the like. While the polymerization reaction time of the monomer components cannot be decided unconditionally since it varies depending on the temperature of polymerization reaction and the like, it is generally about 3-20 hr.

A sulfobetaine polymer can be obtained by polymerizing monomer components as mentioned above. The weight average molecular weight of the sulfobetaine polymer is preferably 3,000-140,000, more preferably 4,000-70,000, further preferably 4,500-56,000. The weight average molecular weight of the sulfobetaine polymer is a value measured based on the method described in the section of the following Example (Preparation Example 1).

The average degree of polymerization of the sulfobetaine polymer is preferably 10-500, more preferably 15-400, further preferably 20-200, for obtaining a protein aggregation inhibitor that maintains lysozyme activity and is superior in a protein aggregation inhibitory effect.

The average degree of polymerization of the sulfobetaine polymer is a value calculated from of the weight average molecular weight measured based on the method described in the section of the following Example (Preparation Example 1), and the molecular weights of the sulfobetaine monomer (particularly, sulfobetaine monomer represented by the formula (II)) and the chain transfer agent (particularly, a compound represented by the formula (III)) used for synthesizing the polymer.

The terminal sulfanyl group-containing sulfobetaine polymer can be produced by reducing the sulfobetaine polymer obtained in the above.

The weight average molecular weight of the terminal sulfanyl group-containing sulfobetaine polymer is preferably 3,000-140,000, more preferably 4,000-70,000, further preferably 4,500-56,000. The weight average molecular weight of the terminal sulfanyl group-containing sulfobetaine polymer can be measured in the same manner as in the method described in the section of the following Example (Preparation Example 1). The weight average molecular weight of the terminal sulfanyl group-containing sulfobetaine polymer can be calculated from the weight average molecular weight of the sulfobetaine polymer (precursor) measured based on the method described in the section of the following Example (Preparation Example 1).

The terminal sulfanyl group-containing sulfobetaine polymer is preferably a terminal sulfanyl group-containing sulfobetaine polymer represented by the formula (IV):

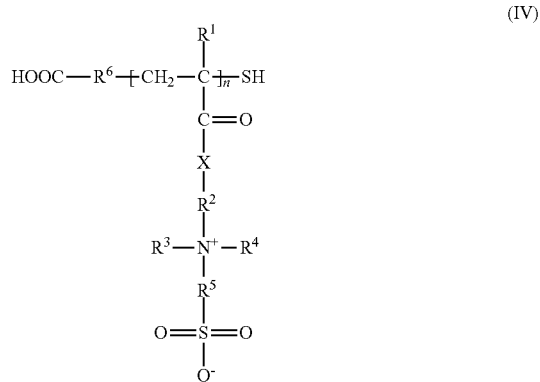

(in the formula (IV), $R^1$ in the number of n are each independently a hydrogen atom or a methyl group, $R^2$ in the number of n are each independently an alkyl group having 1-4 carbon atoms, $R^3$ in the number of n are each independently an alkyl group having 1-4 carbon atoms, $R^4$ in the number of n are each independently an alkyl group having 1-4 carbon atoms, $R^5$ in the number of n are each independently an alkyl group having 1-4 carbon atoms, $R^6$ is an alkylene group having 1-8 carbon atoms and optionally having at least one substituent selected from the group consisting of a cyano group and a phenyl group, X in the number of n are each independently an —NH— group or an —O— group, and n is an average degree of polymerization of 10-500).

n is an average degree of polymerization of the terminal sulfanyl group-containing sulfobetaine polymer represented by the formula (IV). n is preferably 15-400, more preferably 20-200, for obtaining a protein aggregation inhibitor that maintains lysozyme activity and is superior in a protein aggregation inhibitory effect.

The average degree of polymerization of the terminal sulfanyl group-containing sulfobetaine polymer represented by the formula (IV) is the same as the average degree of a sulfobetaine polymer which is a precursor thereof. Therefore, the average degree of polymerization of the terminal sulfanyl group-containing sulfobetaine polymer represented by the formula (IV) can also be calculated by calculating the average degree of polymerization of the sulfobetaine polymer, which is a precursor, as mentioned above. In addition, the average degree of polymerization thereof may also be calculated by measuring the weight average molecular weight of the terminal sulfanyl group-containing sulfobetaine polymer represented by the formula (IV) in the same manner as in the method described in the section of the following Example (Preparation Example 1).

The repeat unit in the terminal sulfanyl group-containing sulfobetaine polymer represented by the formula (IV) may be only one kind or two or more kinds. That is, $R^1$ in the number of n may be the same or different. The same applies to $R^2$ in the number of n, $R^3$ in the number of n, $R^4$ in the number of n, $R^5$ in the number of n and X in the number of n.

It is preferable that the repeat unit in the terminal sulfanyl group-containing sulfobetaine polymer represented by the formula (IV) is only one kind. That is, it is preferable that, in the formula (IV), $R^1$ is a hydrogen atom or a methyl group, $R^2$ is an alkyl group having 1-4 carbon atoms, $R^3$ and $R^4$ are each independently an alkyl group having 1-4 carbon atoms, $R^5$ is an alkyl group having 1-4 carbon atoms, and X is an —NH— group or an —O— group. In this embodiment, $R^6$ is more preferably alkylene having 1-8 carbon atoms.

The explanation of the preferable groups for $R^1$-$R^5$ and X in the formula (IV) is the same as the above-mentioned explanation of the formula (II), and the explanation of preferable groups for $R^6$ in the formula (IV) is the same as the above-mentioned explanation of the formula (III).

For reduction of the aforementioned sulfobetaine polymer, it is desirable to use a reducing agent. Examples of the reducing agent include sodium borohydride, formic acid, formaldehyde, hydrazine, dimethylamine borane and the like. The present invention is not-limited to such exemplification.

The aforementioned reducing agent is generally used as an aqueous solution with a concentration of about 1-20 mass %. The terminal sulfanyl group-containing sulfobetaine polymer can be obtained by mixing the aforementioned sulfobetaine polymer with the aqueous solution and reducing the sulfobetaine polymer contained in the obtained mixture with a reducing agent at room temperature to about 80° C. for about 2-10 hr.

The terminal sulfanyl group-containing sulfobetaine polymer obtained above may be collected by filtration and washed with water where necessary.

Noble metal particles on which a terminal sulfanyl group-containing sulfobetaine polymer is chemisorbed can be produced by mixing the terminal sulfanyl group-containing sulfobetaine polymer obtained above and noble metal particles. The present invention is not limited to such method.

Examples of the noble metal particle include gold, platinum, silver and the like. The present invention is not limited to such exemplification. Among these noble metals, gold is preferable since it improves a protein aggregation inhibitory effect. While an average particle size of the noble metal particle is not particularly limited, it is preferably 1-100 nm, more preferably 1-20 nm, further preferably 1-10 nm, from the aspect of dispersion stability. The average particle size is a value measured by a laser diffraction particle size distribution measuring apparatus [manufactured by SHIMADZU CORPORATION, product number: SALD7000] and means a volume average diameter.

When mixing a terminal sulfanyl group-containing sulfobetaine polymer and noble metal particles, the amount of the noble metal particle per 100 parts by mass of the terminal sulfanyl group-containing sulfobetaine polymer is not particularly limited. It is preferably 10-100 parts by mass, more preferably 20-70 parts by mass, from the aspect of surface coverage.

The temperature at which a terminal sulfanyl group-containing sulfobetaine polymer and noble metal particles are mixed is room temperature to about 80° C., and the mixing time varies depending on the mixing means but is generally about 10-30 hr.

Next, by centrifuging the aforementioned mixture as necessary, the noble metal particles on which the terminal sulfanyl group-containing sulfobetaine polymer is chemisorbed and the terminal sulfanyl group-containing sulfobetaine polymer free from chemisorption can be separated. The centrifuged noble metal particles on which the terminal sulfanyl group-containing sulfobetaine polymer is chemisorbed can be recovered by dispersing the particles in water and filtering the obtained water dispersion.

While the amount of the terminal sulfanyl group-containing sulfobetaine polymer (i.e., terminal sulfanyl group-containing sulfobetaine polymer chemisorbed on noble metal particle) in the protein aggregation inhibitor of the present invention is not particularly limited, it is preferably 5-60 parts by mass, more preferably 10-40 parts by mass, per 100 parts by mass of the noble metal particle, for improving the protein aggregation inhibitory effect and improving dispersion stability.

The protein aggregation inhibitor of the present invention contains noble metal particles on which a terminal sulfanyl group-containing sulfobetaine polymer is chemisorbed, may be constituted only of the aforementioned noble metal particles, and may contain solvents such as water and the like and additive where necessary as long as the object of the present invention is not inhibited.

The noble metal particle on which the terminal sulfanyl group-containing sulfobetaine polymer is chemisorbed is preferably a noble metal particle having, on its surface, a group represented by the formula (I)

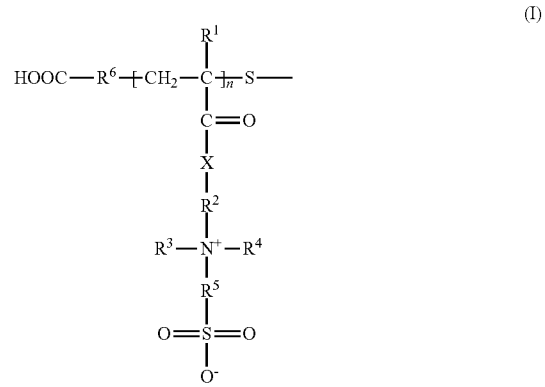

(in the formula (I), $R^1$ in the number of n are each independently a hydrogen atom or a methyl group, $R^2$ in the number of n are each independently an alkyl group having 1-4 carbon atoms, $R^3$ in the number of n are each independently an alkyl group having 1-4 carbon atoms, $R^4$ in the number of n are each independently an alkyl group having 1-4 carbon atoms, $R^5$ in the number of n are each independently an alkyl group having 1-4 carbon atoms, $R^6$ is an alkylene group having 1-8 carbon atoms and optionally having at least one substituent selected from the group consisting of a cyano group and a phenyl group, X in the number of n are each independently an —NH— group or an —O— group, and n is an average degree of polymerization of 10-500).

The explanation of the n (average degree of polymerization) in the formula (I) is the same as that of n (average degree of polymerization) in the formula (IV).

The repeat unit in the group represented by the formula (I) may be only one kind or two or more kinds. That is, $R^1$ in the number of n may be the same or different. The same applies to $R^2$ in the number of n, $R^3$ in the number of n, $R^4$ in the number of n, $R^5$ in the number of n and X in the number of n.

It is preferable that the repeat unit in the group represented by the formula (I) is only one kind. That is, it is preferable that, in the formula (I), $R^1$ is a hydrogen atom or a methyl group, $R^2$ is an alkyl group having 1-4 carbon atoms, $R^3$ and $R^4$ are each independently an alkyl group having 1-4 carbon atoms, $R^5$ is an alkyl group having 1-4 carbon atoms, and X is an —NH— group or an —O— group. In this embodiment, $R^6$ is more preferably alkylene having 1-8 carbon atoms.

The explanation of the preferable groups for $R^1$-$R^5$ and X in the formula (I) is the same as the above-mentioned explanation of the formula (II), and the explanation of preferable groups for $R^6$ in the formula (I) is the same as the above-mentioned explanation of the formula (III).

While the amount of the group represented by the formula (I) in the protein aggregation inhibitor of the present invention is not particularly limited, it is preferably 5-60 parts by mass, more preferably 10-40 parts by mass, per 100 parts by mass of the noble metal particle, for improving the protein aggregation inhibitory effect and improving dispersion stability.

Since the protein aggregation inhibitor of the present invention is superior in a protein aggregation inhibitory effect, it is expected to be used for various applications where inhibition of protein aggregation is desired such as preservative for enzyme, antibody drug, in vivo amyloid aggregation inhibitor and the like.

The present invention provides a method for preventing protein aggregation, including mixing a protein, a solvent or dispersion medium, and the aforementioned protein aggregation inhibitor. In this method, the amount of the noble metal particle with the terminal sulfanyl group-containing sulfobetaine polymer chemisorbed thereon or the amount of the noble metal particle having a group represented by the formula (I) on the surface is preferably 0.01-10 parts by mass, more preferably 0.1-1 parts by mass, per 1 part by mass of the protein. The aforementioned "amount of the noble metal particle with the terminal sulfanyl group-containing sulfobetaine polymer chemisorbed thereon" means a "total of the amount of the chemisorbed terminal sulfanyl group-containing sulfobetaine polymer and the amount of the noble metal particle", and the "amount of the noble metal particle having a group represented by the formula (I) on the surface" means a "total of the amount of the group represented by the formula (I) and the amount of the noble metal particle".

Examples of the solvent or dispersion medium include phosphate buffered saline (PBS), water, tris buffer and the like.

Examples of the protein include lysozyme, albumin, globulin, prolamin, glutelin, cytokine, insulin, antibody, membrane protein, glycoprotein and the like.

The content of a protein in a mixture containing the protein, a solvent or dispersion medium, and the aforementioned protein aggregation inhibitor is preferably 0.001-20 mass %, more preferably 0.01-10 mass %.

EXAMPLES

The present invention is explained in more detail in the following by referring to Examples. However, the present invention is not limited to the Examples alone.

Preparation Example 1

In a 1 L flask provided with a stirring rod, a dimroth, a thermometer and a nitrogen gas introducing tube, 3-[(3-acrylamidopropyl)dimethylammonio]propane-1-sulfonate (12 mmol), 2-(dodecylthiocarbonothioylthio)-2-methylpropionic acid (0.6 mmol) and azobisisobutyronitrile (0.12 mmol) as a polymerization initiator were dissolved in a mixed solvent (60 mL) of methanol (45 mL) and water (15 ml) to give a solution. The obtained solution was placed in a flask, the contents of the flask were heated to 70° C. while introducing a nitrogen gas into the flask, and the mixture was stirred for 1 hr. Thereafter, the monomer components in the flask were polymerized for 6 hr to give a reaction mixture. The obtained reaction mixture was collected by filtration, washed with methanol and water and dried to give a sulfobetaine polymer.

Then, the average degree of polymerization of the obtained sulfobetaine polymer was examined by gel permeation chromatography (hereinafter to be referred to as GPC) analysis apparatus [manufactured by Phenomenex, Ink., trade name: BioSeps2000] and high performance liquid chromatography data system [manufactured by SHIMADZU CORPORATION, differential refractometer detector]. As a result, the average degree of polymerization of the sulfobetaine polymer was 6,000. Using the weight average molecular weight, the molecular weight (278) of a sulfobetaine monomer (i.e., 3-[(3-acrylamidopropyl)dimethyl-ammonio]propane-1-sulfonate) and the molecular weight (364) of a compound represented by the formula (III) (i.e., 2-(dodecylthiocarbonothioylthio)-2-methylpropionic acid), the average degree of polymerization (n) was calculated to be 20 from the following formula: n=(6,000-364)/278=20.

When the average degree of polymerization of the sulfobetaine polymer obtained above was examined by GPC, 0.1 M aqueous sodium bromide solution (pH:7.4) was used as a developing solution. In addition, pullulan manufactured by Showa Denko K.K. was used as the standard solution.

Then, the sulfobetaine polymer (10 g) obtained above was added to a 5% aqueous sodium borohydride solution (100 g) at ordinary temperature, and the mixture was stirred for 4 hr to give a reaction solution containing a terminal sulfanyl group-containing sulfobetaine polymer. The weight average molecular weight of the obtained terminal sulfanyl group-containing sulfobetaine polymer was calculated to be 5,800 from the weight average molecular weight of the sulfobetaine polymer which is a precursor thereof.

The reaction solution containing the terminal sulfanyl group-containing sulfobetaine polymer obtained above was filtered to recover the produced terminal sulfanyl group-containing sulfobetaine polymer, and the recovered terminal sulfanyl group-containing sulfobetaine polymer was purified by washing with water.

Example 1

The terminal sulfanyl group-containing sulfobetaine polymer (100 g) obtained in Preparation Example 1 and fine gold particles (average particle size: 5 nm) (30 g) were mixed and the obtained mixture was stirred at room temperature for 24 hr, whereby a mixture containing fine gold particles having a group represented by the formula (I) on the surface was obtained.

The mixture containing fine gold particles having a group represented by the formula (I) on the surface obtained above was placed in a centrifugal separator and stirred at room temperature, rotating speed 12,000 rpm for 180 min to separate the fine gold particles having a group represented by the formula (I) on the surface. The separated fine gold particles mentioned above were dispersed in water, and the aforementioned fine gold particles were recovered by filtration and used as a protein aggregation inhibitor. The amount of the group represented by the formula (I) (i.e., amount of chemisorbed terminal sulfanyl group-containing sulfobetaine polymer) in the obtained protein aggregation inhibitor was 25 parts by mass per 100 parts by mass of the fine gold particles.

The fine gold particles having a group represented by the formula (I) on the surface were added to water to prepare a dispersion with a content of the aforementioned fine gold particles of 1 mass %. Lysozyme-containing phosphate buffered saline (PBS) was add to and mixed with the obtained dispersion to give a mixture (amount of fine gold particles having a group represented by the formula (I) on the surface per 1 part by mass of the protein (lysozyme) 0.56 parts by mass, content of protein (lysozyme) in the mixture: 0.05 mass %). The obtained mixture was visually observed to find no aggregation of lysozyme.

Then, the mixture obtained above was heated at 90° C. for 30 min and cooled to room temperature. The cooled mixture was stirred at room temperature, rotating speed 12,000 rpm for 30 min. The supernatant liquid was recovered, the absorbance at a wavelength of 280 nm was measured by a spectrophotometer [SHIMADZU CORPORATION, product number: UV-1600PC], and the amount of lysozyme dissolved in the supernatant liquid was quantified from the absorbance at 280 nm derived from lysozyme.

The protein aggregation inhibitory ratio (%) was determined from the amount of the dissolved lysozyme quantified above and based on the following formula:

[protein aggregation inhibitory ratio (%)]=([dissolved lysozyme amount]÷[amount of lysozyme added to dispersion])×100

As a result, the protein aggregation inhibitory ratio was 13%.

Comparative Example 1

Using the terminal sulfanyl group-containing sulfobetaine polymer obtained in Preparation Example 1 as a protein aggregation inhibitor and in the same manner as in Example 1, a protein aggregation inhibitory effect was examined. As a result, the protein aggregation inhibitory ratio was 0.02%.

Comparative Example 2

Using fine gold particles (average particle size: 5 nm) as a protein aggregation inhibitor and in the same manner as in Example 1, a protein aggregation inhibitory effect was examined. As a result, the protein aggregation inhibitory ratio was 9.0%.

From the results of Example 1 and Comparative Examples 1-2, it is clear that the protein aggregation inhibitor (i.e., fine gold particles having a group represented by the formula (I) on the surface) obtained in Example 1 is particularly remarkably superior in the protein aggregation inhibitory effect as compared to the protein aggregation inhibitor composed of the terminal sulfanyl group-containing sulfobetaine polymer obtained in Comparative Example 1, and the protein aggregation inhibitor composed of fine gold particles obtained in Comparative Example 2.

INDUSTRIAL APPLICABILITY

The protein aggregation inhibitor of the present invention can maintain lysozyme activity and effectively inhibit protein aggregation even without using a surfactant. Therefore, it is expected to be used for various applications where inhibition of protein aggregation is desired such as preservative for enzyme, antibody drug, in vivo amyloid aggregation inhibitor and the like.

Therefore, the protein aggregation inhibitor of the present invention is expected to be used in various fields such as food processing field, antibody drug field, transplantation therapy field, enzyme production field, pharmaceutical-related field and the like.

This application is based on a patent application No. 2016-130596 filed in Japan, the contents of which are incorporated in full herein.

The invention claimed is:
1. A protein aggregation inhibitor for use in preventing aggregation of a protein, the inhibitor comprising
a terminal sulfanyl group-containing sulfobetaine polymer having a repeat unit derived from a sulfobetaine monomer represented by the formula (II):

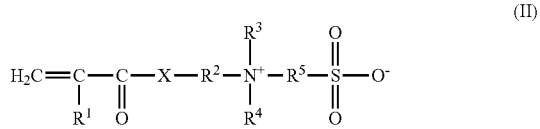
(II)

(in the formula (II), $R^1$ is a hydrogen atom or a methyl group, $R^2$ an alkyl group having 1-4 carbon atoms, $R^3$ and $R^4$ are each independently an alkyl group having 1-4 carbon atoms, $R^5$ is an alkyl group having 1-4 carbon atoms, and X is an —NH— group or an —O— group), and
a noble metal particle, wherein the terminal sulfanyl group-containing sulfobetaine polymer is chemisorbed on the noble metal particle by the sulfanyl group,
wherein the terminal sulfanyl group-containing sulfobetaine polymer is present in an amount of 5-60 parts by mass per 100 parts by mass of the noble metal particle.

2. The protein aggregation inhibitor according to claim 1, wherein the terminal sulfanyl group-containing sulfobetaine polymer further has a carboxyl group.

3. The protein aggregation inhibitor according to claim 2, wherein the noble metal is gold.

4. The protein aggregation inhibitor according to claim 2, wherein the noble metal particle has an average particle size of 1-100 nm.

5. The protein aggregation inhibitor according to claim 1, wherein the terminal sulfanyl group-containing sulfobetaine polymer is obtained by polymerizing monomer components comprising a sulfobetaine monomer represented by the formula (II) and a compound represented by the formula (III):

$$HOOC-R^6-S-C(=S)-S-R^7 \qquad (III)$$

(in the formula (III), $R^6$ is an alkylene group having 1-8 carbon atoms and optionally having at least one substituent selected from the group consisting of a cyano group and a phenyl group, and $R^7$ is an alkyl group having 1-18 carbon atoms and optionally having at least one substituent selected from the group consisting of a carboxyl group and a phenyl group) to prepare a sulfobetaine polymer, and reducing the obtained sulfobetaine polymer.

6. The protein aggregation inhibitor according to claim 5, wherein the noble metal is gold.

7. The protein aggregation inhibitor according to claim 5, wherein the noble metal particle has an average particle size of 1-100 nm.

8. The protein aggregation inhibitor according to claim 1, wherein the terminal sulfanyl group-containing sulfobetaine polymer has a weight average molecular weight of 3,000-140,000.

9. The protein aggregation inhibitor according to claim 8, wherein the noble metal is gold.

10. The protein aggregation inhibitor according to claim 8, wherein the noble metal particle has an average particle size of 1-100 nm.

11. The protein aggregation inhibitor according to claim 1, wherein the noble metal is gold.

12. The protein aggregation inhibitor according to claim 11, wherein the noble metal particle has an average particle size of 1-100 nm.

13. The protein aggregation inhibitor according to claim 1, wherein the noble metal particle has an average particle size of 1-100 nm.

14. A protein aggregation inhibitor for use in preventing aggregation of a protein, comprising a noble metal particle having, on its surface, a group represented by the formula (I):

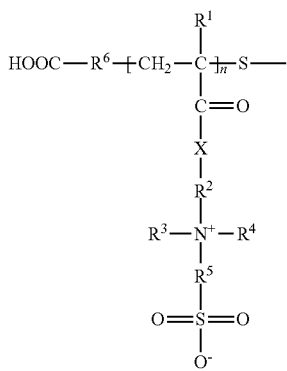

(I)

(in the formula (I), $R^1$ in the number of n are each independently a hydrogen atom or a methyl group, $R^2$ in the number of n are each independently an alkyl group having 1-4 carbon atoms, $R^3$ in the number of n are each independently an alkyl group having 1-4 carbon atoms, $R^4$ in the number of n are each independently an alkyl group having 1-4 carbon atoms, $R^5$ in the number of n are each independently an alkyl group having 1-4 carbon atoms, $R^6$ is an alkylene group having 1-8 carbon atoms and optionally having at least one substituent selected from the group consisting of a cyano group and a phenyl group, X in the number of n are each independently an —NH— group or an —O— group, and n is an average degree of polymerization of 10-500), wherein the group represented by the formula (I) is present in an amount of 5-60 parts by mass per 100 parts by mass of the noble metal particle.

15. The protein aggregation inhibitor according to claim 14, wherein, in the formula (I), $R^1$ is a hydrogen atom or a methyl group, $R^2$ an alkyl group having 1-4 carbon atoms, $R^3$ and $R^4$ are each independently an alkyl group having 1-4 carbon atoms, $R^5$ is an alkyl group having 1-4 carbon atoms, $R^6$ is alkylene having 1-8 carbon atoms, and X is an —NH— group or an —O— group.

16. The protein aggregation inhibitor according to claim 15, wherein the noble metal is gold.

17. The protein aggregation inhibitor according to claim 15, wherein the noble metal particle has an average particle size of 1-100 nm.

18. A method for producing a protein aggregation inhibitor for use in preventing aggregation of a protein, the method comprising polymerizing monomer components comprising a sulfobetaine monomer represented by the formula (II):

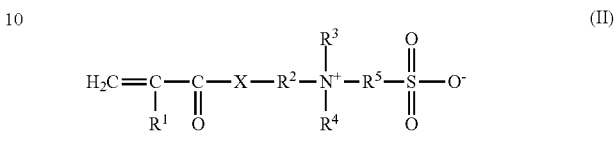

(II)

(in the formula (II), $R^1$ is a hydrogen atom or a methyl group, $R^2$ an alkyl group having 1-4 carbon atoms, $R^3$ and $R^4$ are each independently an alkyl group having 1-4 carbon atoms, $R^5$ is an alkyl group having 1-4 carbon atoms, and X is an —NH— group or an —O— group), and a compound represented by the formula (III):

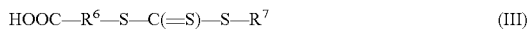

(III)

(in the formula (III), $R^6$ is an alkylene group having 1-8 carbon atoms and optionally having at least one substituent selected from the group consisting of a cyano group and a phenyl group, and $R^7$ is an alkyl group having 1-18 carbon atoms and optionally having at least one substituent selected from the group consisting of a carboxyl group and a phenyl group) to prepare a sulfobetaine polymer, reducing the obtained sulfobetaine polymer to prepare a terminal sulfanyl group-containing sulfobetaine polymer, and mixing the obtained terminal sulfanyl group-containing sulfobetaine polymer and a noble metal particle.

19. The protein aggregation inhibitor according to claim 14, wherein the noble metal is gold.

20. The protein aggregation inhibitor according to claim 14, wherein the noble metal particle has an average particle size of 1-100 nm.

* * * * *